United States Patent
Manchester et al.

(10) Patent No.: US 10,899,997 B2
(45) Date of Patent: Jan. 26, 2021

(54) METHODS FOR EXTRACTING ESSENTIAL OILS, TERPENES, TERPENOIDS AND OTHER ORGANIC MATTER FROM PLANTS; AND RELATED SYSTEMS AND DEVICES

(71) Applicant: Hammer Industrial and Hydraulics, LLC, Seattle, WA (US)

(72) Inventors: Griffin Manchester, Seattle, WA (US); Kurt Manchester, Seattle, WA (US); Daniel Hay, Seattle, WA (US)

( * ) Notice: Subject to any disclaimer, the term of this patent is extended or adjusted under 35 U.S.C. 154(b) by 38 days.

(21) Appl. No.: 15/667,354

(22) Filed: Aug. 2, 2017

(65) Prior Publication Data

US 2018/0037845 A1    Feb. 8, 2018

Related U.S. Application Data

(60) Provisional application No. 62/370,573, filed on Aug. 3, 2016.

(51) Int. Cl.

| | | |
|---|---|---|
| *A61K 36/00* | (2006.01) | |
| *C11B 9/02* | (2006.01) | |
| *C12C 3/04* | (2006.01) | |
| *C12C 3/00* | (2006.01) | |
| *A23L 2/56* | (2006.01) | |
| *C12C 3/02* | (2006.01) | |
| *B01D 11/02* | (2006.01) | |
| *B01D 11/04* | (2006.01) | |
| *B01F 9/00* | (2006.01) | |
| *B01F 15/00* | (2006.01) | |
| *B07B 1/22* | (2006.01) | |
| *C07C 7/00* | (2006.01) | |
| *C07C 11/18* | (2006.01) | |
| *C12C 3/10* | (2006.01) | |

(52) U.S. Cl.
CPC ............... *C11B 9/022* (2013.01); *A23L 2/56* (2013.01); *B01D 11/0273* (2013.01); *B01D 11/0484* (2013.01); *B01F 9/0005* (2013.01); *B01F 15/00538* (2013.01); *B07B 1/22* (2013.01); *C07C 7/005* (2013.01); *C07C 11/18* (2013.01); *C11B 9/02* (2013.01); *C12C 3/00* (2013.01); *C12C 3/02* (2013.01); *C12C 3/04* (2013.01); *C12C 3/10* (2013.01)

(58) Field of Classification Search
None
See application file for complete search history.

(56) References Cited

U.S. PATENT DOCUMENTS

| 2,833,652 A | 5/1958 | Naatz | |
|---|---|---|---|
| 3,787,586 A * | 1/1974 | Hokanson | ................. C12C 3/04 426/486 |

FOREIGN PATENT DOCUMENTS

| GB | 1166386 | 10/1969 | |
|---|---|---|---|
| GB | 1166386 A * | 10/1969 | ............... C12C 3/00 |
| WO | 00/06691 A1 | 2/2000 | |

OTHER PUBLICATIONS

Cunha et al. (2018) Carbon Dioxide Use in High-Pressure Processes. http://dx.doi.org/10.5772/Intechopen.71151. 31 pages (Year: 2018).*
Formato et al. (2013) J. of Supercritical Fluids, 84:113-120. (Year: 2013).*
Vollbrecht et al. (1982) Chemistry and Industry, 397-399 (Year: 1982).*
Almaguer et al. (2014) J. Inst. Brew. 120: 289-314. (Year: 2014).*
Hrncic et al.(2019) Nutrients 11, 257 (37 pages) (Year: 2019).*
Website document entitled "Rock Tumbler Grit" (available at https://www.smarterhobby.com/rock-tumbling/rock-tumbler-grit/). Downloaded Apr. 3, 2020. (Year: 2020).*

* cited by examiner

*Primary Examiner* — Russell G Fiebig
(74) *Attorney, Agent, or Firm* — Janeway Patent Law PLLC; John M. Janeway

(57) ABSTRACT

A method for extracting resins and oils from a plant includes: 1) tumbling, inside a container at a temperature of at most 50 degrees Fahrenheit with a tumbler, plant fibers having one or more portions that contain resins and/or oils; 2) colliding the tumbler with the plant fibers to release the one or more portions that contain resins and/or oils from the remainder of the plant fibers; and 3) segregating the one or more portions that contain resins and/or oils from the remainder of the plant fibers.

6 Claims, 6 Drawing Sheets

METHODS FOR EXTRACTING ESSENTIAL OILS, TERPENES, TERPENOIDS AND OTHER ORGANIC MATTER FROM PLANTS; AND RELATED SYSTEMS AND DEVICES

CROSS REFERENCE TO RELATED APPLICATION AND CLAIM OF PRIORITY

This application claims priority from commonly owned U.S. Provisional Patent Application 62/370,573 filed 3 Aug. 2016, and titled "Methods For Extracting Essential Oils, Terpenes, Terpenoids And Other Organic Matter From Plants; And Related Systems And Devices", and incorporated by reference.

BACKGROUND

Essential oils and resins of a plant, which often include terpenes and terpenoids, are used for a variety of reasons. Some, such as the essential oils and resins from basil, lavender and frankincense, are used to enhance the aroma of a product, such as a perfume, or as an antiseptic to help heal or sooth skin. Some, such as the essential oils and resins from garlic and tea tree, are used as an antibiotic to help heal a wound. Some, such as the essential oils and resins from cinnamon, cloves and peppermint are used as an anesthetic. And some, such as the essential oils and resins from hops are used to flavor and preserve beverages such as beer.

Essential oils are typically volatile or easily evaporate at normal temperatures when exposed to the environment, and terpenes and terpenoids are typically reactive with other compounds when exposed to heat, ultra-violet light, and/or oxygen. Because of this, the extraction of a plant's essential oils and/or resins is often done quickly after the plant has been harvested, before the harvested plant, its essential oils, and/or its resins can decay and adversely affect the quality of the essential oils, terpenes and terpenoids. Such extraction is typically done by distillation, expression, or solvent extraction. Distillation involves heating the plant with steam or some other material to force the essential oils or resins out of the plant's cellular structure, and then capturing the oil or resin. Expression involves mechanically pressing the essential oils or resins out of the plant's cellular structure. And, solvent extraction involves exposing the essential oil or resin by breaking down the plant's cellular structure with a solvent.

Each of these forms of extraction work well if you want to isolate a specific essential oil, terpene or terpenoid contained within the plant. But, sometimes one wants to concentrate the essential oil and resins contained in a plant, not completely isolate it from the whole plant—i.e., remove some or most of a plants cellular structure but not all of the plant's cellular structure. This is especially true with hops and its use in the production of beer. Brewers use many of the hop's terpenes, terpenoids and essential oils as well as other parts of the hop to flavor and preserve their beer. The terpenes, terpenoids and essential oils contained in the hop's flower (the hop's seed cone or strobili) include alpha acids, such as humulone, cohumulone, and adhumulone; beta acids, such as lupulone, colupulone, and adlupulone; and humulene, myrcene, and caryophllene. Alpha acids add bitterness to a beer to offset the sweetness produced from grain during the brewing process, help prevent bacterial growth during and after the brewing process, and promote the growth of the yeast that converts starch and sugar into alcohol. Beta acids also add bitterness to the beer. Essential oils add flavor and aroma to the beer. Because there are many different species of hops, each having a unique combination of alpha acids, beta acids and essential oils, there are many different flavor combinations available to a brewer as well as anti-bacterial functions.

Figure 1:
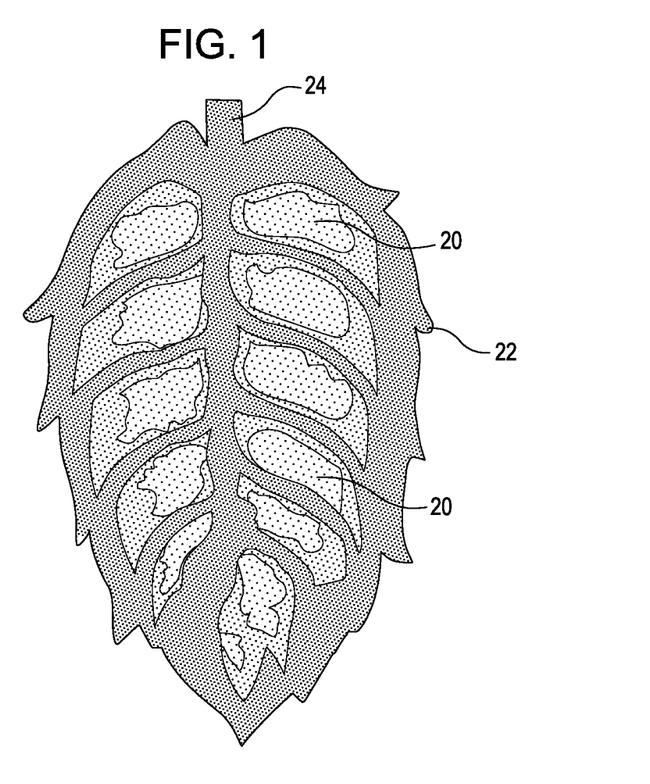
FIG. 1 shows a cross-sectional view of a hop's cone.

FIG. 1 shows a cross-section of a typical hop flower that contains the alpha acids, beta acids and essential oils that most brewers desire. Each hop flower includes a plurality of lupulin glands 20, in which the alpha and beta acids and the essential oils are found, surrounded by leaf-like structures called bracts 22, both of which are anchored to the strig 24. Ideally, a brewer wants the lupulin gland intact until he puts the hops into the wort—the sugar-rich mixture of mashed grains and water that can then be fermented by the yeast. In the wort, the lupulin gland breaks down and releases the alpha acids, beta acids and essential oils that it contains. By keeping the alpha acids, beta acids and essential oils contained within the lupulin gland for as long as possible, one can preserve the freshness of desired alpha acids, beta acids and essential oils.

Brewers brew beer continuously throughout the year, but the flowers of hops are harvested once a year typically in August or September. So, most of the hops harvest is preserved for future use. Hops are typically preserved by drying them whole in a cool, dark warehouse. Once dried, they are often pelletized (compressed) and packaged in an air-tight container that has most of the air removed.

Unfortunately, this process for preserving the flowers allows some of the alpha acids, beta acids and essential oils to breakdown, and also allows some of the essential oils to evaporate out of the flower. During the drying process, the whole flower is dried in low-humidity air that includes oxygen for a week or more. The oxygen often reacts with each of the acids and oils and adversely changes their chemical composition and molecular structure. And because the whole flower is typically dried, there is more surface area exposed to the oxygen in the air which allows more molecules to react with the oxygen. To reduce the time spent drying the flowers, the flowers are typically heated to a temperature that does not exceed 140 degrees Fahrenheit. This reduces the drying time to three days, but promotes isomerization (a change in molecular structure) of the alpha acids, which adversely affects the quality of the alpha acids desired for beer.

Thus, there is a need for a process that preserves the desirable alpha acids, beta acids and essential oils that fresh hops contain for future use.

SUMMARY

In an aspect of the invention, a method for extracting resins and oils from a plant includes: 1) tumbling, inside a container at a temperature of at most 50 degrees Fahrenheit with a tumbler, plant fibers having one or more portions that contain resins and/or oils; 2) colliding the tumbler with the plant fibers to separate the one or more portions that contain resins and/or oils from the remainder of the plant fibers; and 3) segregating the one or more portions that contain resins and/or oils from the remainder of the plant fibers.

By tumbling the plant fibers with a tumbler and colliding the tumbler into the plant fibers, portions of the plant fibers that contain resins and oils, which include terpenes, terpenoids and essential oils, are separated from the remainder of the plant fiber without causing much damage to the portion of the plant fibers that includes the resins and oils. For hop flowers, this allows one to separate much of the unwanted portion of the hops flower—the bract and strig—from the desired portion—the lupulin gland and the alpha acids, beta acids and essential oils contained in it—with minimal damage to the lupulin gland. When the hop flowers and the tumbler are tumbled at a temperature of at most 50 degrees Fahrenheit, the alpha acids in the lupulin gland are discouraged from isomerization. If the hop flowers are tumbled with the tumbler when the hop flowers are wet (fresh) or within a couple of days after being harvested, and the separated lupulin glands are packaged and stored in a room without light and oxygen, then the lupulin glands and the acids and oils that they contain can remain very close to fresh if not fresh until they're used to brew beer.

In another aspect of the invention, a method for extracting resins and oils from a plant includes: 1) tumbling, inside a container having an atmosphere that does not include oxygen with a tumbler, plant fibers having one or more portions that contain resins and/or oils; 2) colliding the tumbler with the plant fibers to separate the one or more portions that contain resins and/or oils from the remainder of the plant fibers; and 3) segregating the one or more portions that contain resins and/or oils from the remainder of the plant fibers.

In still another aspect of the invention, a method for extracting resins and oils from a plant includes; 1) tumbling, inside a container having an atmosphere that does not include ultraviolet light with a tumbler, plant fibers having one or more portions that contain resins and/or oils; 2) colliding the tumbler with the plant fibers to separate the one or more portions that contain resins and/or oils from the remainder of the plant fibers; and 3) segregating the one or more portions that contain resins and/or oils from the remainder of the plant fibers.

In yet another aspect of the invention, a device to extract resins and oils from a plant includes a container, a chassis, a motor, and a component operable to cool the container. The container includes a body that defines a cavity and is operable to hold inside the cavity: 1) plant fibers having one or more portions that contain resins and/or oils, and 2) a tumbler. The container's body has a first region that defines an opening through which the cavity may be accessed, and a second region. The chassis is coupled to the container and operable to support the container while the container rotates about an axis. The motor is operable to rotate the body about the axis. And, the component is operable to cool the cavity of the container's body such that: 1) when the body holds the plant fibers and the tumbler inside the cavity, and 2) the motor rotates the body to tumble the plant fibers with the tumbler, the plant fibers are cooled to at least 50 degrees Fahrenheit.

DETAILED DESCRIPTION

Figure 2:
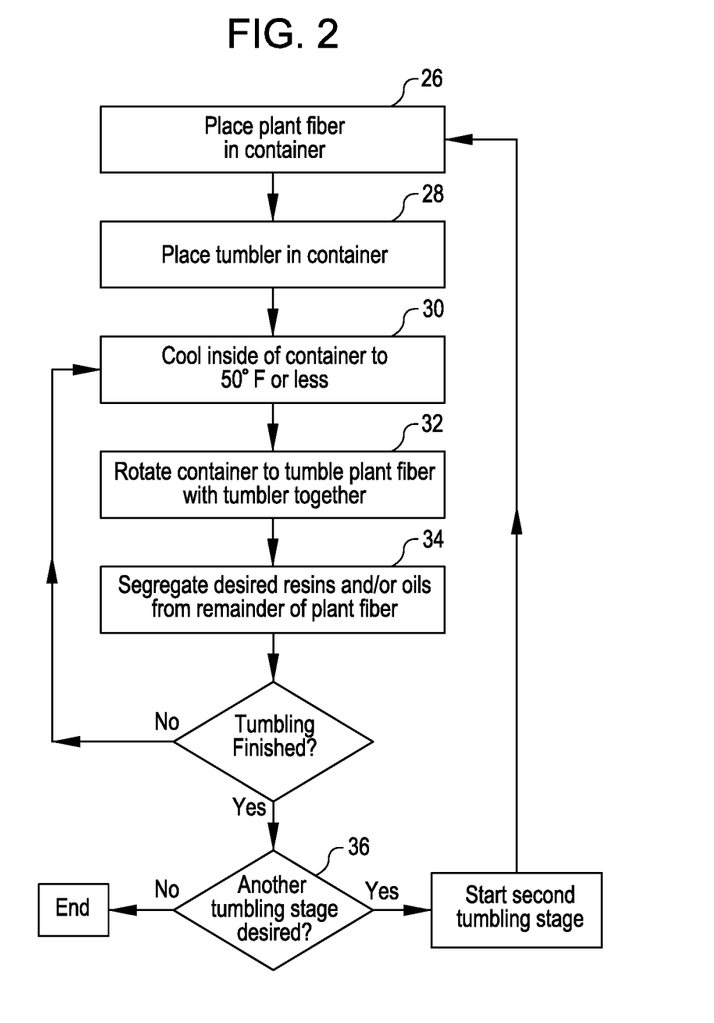
FIG. 2 shows a flow chart of a process for extracting resins and oils from a plant, such as hops, according to an embodiment of the invention.

FIG. 2 shows a flow chart of a process for extracting resins and oils from a plant according to an embodiment of the invention. The process may be used to extract resins and/or oils from any desired plant and works especially well with extracting from hop flowers (hop seed cones or strobiles) the lupulin glands and the alpha acids, beta aids and essential oils that the glands contain. For example, the process may be used to extract essential oils and other terpenes and terpenoids produced by lavender. The process includes: 1) tumbling, inside a container at a temperature of at most 50 degrees Fahrenheit (F) with a tumbler, plant fibers having one or more portions that contain resins and/or oils; 2) colliding the tumbler with the plant fibers to separate the one or more portions that contain resins and/or oils from the remainder of the plant fibers; and 3) segregating the one or more portions that contain resins and/or oils from the remainder of the plant fibers.

As the tumbler and plant fibers tumble in the container, they collide into each other and into the container. These collisions break the plant fibers into smaller pieces that allow easier access to the organic material of the plant fibers that contain or include the desired essential oils, terpenes and/or terpenoids. When the collisions of the plant fibers and tumbler occur at a cool temperature, the desired essential oils, terpenes and/or terpenoids in the smaller portions of the plant fibers are less likely to be damaged and/or lost through evaporation. The cool temperature reduces the volatility of the desired essential oils causing less oil to evaporate during extraction. The cool temperature also discourages isomerization of chemical molecules in the desired terpenes and terpenoids. In other words, while the chaff and other undesirable plant fibers are separated from the desired organic material of the plant, less of the desired organic material, such as essential oils, terpenes and terpenoids, is lost during the process.

For hop flowers, tumbling the plant fibers with a tumbler at a temperature of at most 50 degrees F. allows one to separate much of the unwanted portion of the hops flower—the bract and strig—from the desired portion—the lupulin gland and the alpha acids, beta acids and essential oils contained in it—with minimal damage to the lupulin gland. When the hop flowers and the tumbler are tumbled at a temperature of at most 50 degrees F., the alpha acids in the lupulin gland are discouraged from isomerization. If the hop flowers are tumbled with the tumbler when the hop flowers are wet (fresh) or within a couple of days after being harvested, and the segregated lupulin glands are packaged and stored in a room without light and oxygen, then the lupulin glands and the acids and oils that they contain can remain very close to fresh if not fresh until they're used to brew beer. If the hop flowers are tumbled with the tumbler when the flowers are dry (previously dried and/or stored for more than a couple of days), then the lupulin glands and the acids and oils that they contain can remain very close to the degree of freshness that they had before they were processed.

Still referring to FIG. 2, the first step 26 in the process includes placing plant fibers (here hop flowers) that contain desired essential oils, terpenes, and terpenoids in a container. The container (discussed in greater detail in conjunction with FIGS. 6 and 7) includes a cavity configured to hold the plant fibers and allow the plant fibers to tumble within the cavity when the container is rotated about a longitudinal axis (shown in FIGS. 6 and 7) that is aligned with the container's central axis.

The next step 28 includes placing a tumbler in the container. The combined volume of the plant fibers and tumblers in the container's cavity may be any desired volume that allows one to efficiently process the plant fibers. For example, in this and other embodiments, the combined volume is less than half of the volume of the container's cavity. In addition, the tumbler may be configured as desired and the process may use any desired number of tumblers that will cause enough, substantial collisions with the plant fibers to quickly separate most of the portions of the plant fibers that contain the desired essential oils, terpenes, and terpenoids from the remaining portions of the plant fibers. For example, in this and other embodiments of the process the tumbler includes about fifty cylinders each having a length of about one inch and a diameter of about ⅓ of an inch. With this number of tumblers configured in this manner, about three pounds of dried hop flowers may be sufficiently processed in about fifteen minutes.

The tumbler may also be made of any desired material. For example, the tumbler may be made of a metal such as nickel to provide a substantial impact force when colliding with the plant fibers and that may also provide a catalyst for promoting a chemical reaction to help segregate the desired essential oils, terpenes and terpenoids, and/or protecting them during the process. In another example, the tumbler may be made of wood or some other softer and lighter material to provide less impact force when colliding with the plant fibers. As the weight of the tumbler increases, the impact force generated when the tumbler collides with the plant fibers increases. So, if the plant fibers being processed are hard or tough to break, then one may want to use a heavier tumbler. And, if the plant fibers being processed are soft or easy to break, then one may want to use a lighter tumbler. Likewise, the tumbler's configuration also effects how the tumbler breaks the plant fibers. When the tumbler includes one or more sharp edges, the breaks in the plant fibers tend to be clean cuts. And, when the tumbler includes one or more rounded or blunt edges, the breaks in the plant fibers tend to be crushed or smashed. So, depending on how the particular plant fibers contain the desired essential oils, terpenes, and terpenoids, one may use a tumbler with one or sharp edges, one or more blunt edges, or any combination of the two.

Other embodiments are possible. For example, the size of each tumbler may be larger than the 1-inch by 0.33-inch cylindrical tumblers, and may be configured into other geometric shapes and well as an amorphous shape. In other embodiments, the size and shape of each of the tumblers may vary, that is, may not be substantially uniform. And, in other embodiments the total number of tumblers used may be more or fewer than fifty.

The next step 30 includes cooling the inside of the container to 50 degrees F. or less to keep the temperature of the plant fibers at 50 degrees F. or less while they collide with the tumblers. This may be accomplished in any desired manner. For example, in this and other embodiments the tumbler is a solid that sublimates at the ambient temperature to cool the plant fibers to a tumbling temperature that is less than 50 degrees F. More specifically, in this and other embodiments the tumbler includes many pellets of dry ice (frozen $CO_2$). The pellets are cylindrical in shape and are approximately 1-inch long by 0.33 inches in diameter. For processing hop flowers, these sublimating, solid tumblers work well. In other embodiments, the temperature in the cavity inside the container, and thus the plant fibers being processed, may be cooled by injecting cool air into the container's cavity. The cool air may be generated by any conventional technique, such as a thermodynamic refrigeration cycle, and then directed into the container's cavity. In still other embodiments, the cavity inside the container may be cooled by packing ice or some other cool material around the container's cavity.

The next step 32 includes rotating the container to tumble the plant fibers with the tumblers and cause the tumblers to collide with the plant fibers. The container may be rotated at any desired speed that allows one to efficiently process the plant fibers. For efficient processing to occur, the tumbler and plant fibers should tumble inside the container's cavity, much like clothes in a dryer. If the container rotates too fast, then the tumbler and/or plant fibers are simply thrown against the walls of the cavity and held there by centrifugal force. When this occurs, the tumbler and plant fibers don't collide with each other and the plant fibers are not broken into small portions. And, if the container rotates too slow, then the tumbler and/or plant fibers simply slide along the walls of the cavity. In this and other embodiments, the container is rotated at about 60 revolutions per minute. For processing hop flowers, this rotational speed works well. When processing heavier plant fibers or when using a heavier tumbler, a faster rotational speed may be used.

The next step 34 includes segregating the portions of the plant fibers that contain the desired essential oils, terpenes and/or terpenoids from the remaining portions of the plant fibers that don't. Segregating the desired portions of the plant fibers from the undesired ones may be accomplished in any desired manner. For example, in this and other embodiments, a screen having a mesh size that allows the desired plant fiber to pass through it and into a receptacle, and not allow the undesired plant fibers to pass through it into the receptacle is used to filter out the undesired plant fibers. For processing hop flowers, a screen having a mesh size of about 0.125 inches works well. In other embodiments, segregating the desired plant fibers from the undesired plant fibers may be performed by vibrating the container or blowing air up through the plant fibers to urge the lighter and/or less dense portions of the plant fibers to rise above the heavier and/or more dense portions. This works well if the weight or density of each of the desired portions of the processed plant fibers is less than the weight or density of the undesired portions.

The next step 36 in the process includes determining whether the segregated desired plant fibers should proceed through another tumbling stage. In some situations, a single-stage process—a process where the plant fibers tumble and collide with a tumbler, and then are segregated from the undesired plant fibers—may be sufficient to extract the essential oils, terpenes and terpenoids from plant fibers. But, in other situations, a multiple-stage process—a process where two or more single-stage processes are performed on the desired plant fibers—may be desired. In such situations, one may simply take the desired plant fibers that were segregated during the first process and may process them again through another single-stage process. For example, in this and other embodiments, the desired plant fibers may be tumbled with a tumbler under the same tumbling conditions as the first process, but may be segregated from undesired plant fibers with a screen having a finer mesh. After this second processing stage is completed, the desired plant fibers may have a higher concentration of the desired essential oils, terpenes and terpenoids, than the desired plant fibers after the first processing stage. For processing hop flowers, multiple-stage processing works well. For other plants, a single processing stage may suffice.

Other embodiments are possible. For example, the second or subsequent processing stage may include tumbling the desired plant fibers with a tumbler and/or under tumbling conditions that are different than the tumbler and the tumbling conditions in the first processing stage.

In an example of the process, hop flowers were tumbled with dry ice through three stages. In the first stage, three pounds of hop flowers as picked in the fields at an ambient temperature of 82 degrees F. were tumbled for fifteen minutes with six pounds of dry ice (in the form of 50 cylindrical pellets 1 inch long by 0.33 inches in diameter) in a container having a mesh size of 0.125 inches and at a temperature of 49 degrees F. The product that passed through the mesh, out of the container, and into the receptacle, was retrieved and then tumbled again for fifteen minutes with five pounds of dry ice (in the same form) in another container with a mesh size of 800 microns. The product that passed through the mesh, out of this container, and into the housing, was retrieved and then tumbled again for sixteen minutes with five pounds of dry ice (in the same form again) in a third container with a mesh size of 300 microns. The product that passed through the mesh and out of this third container had a temperature of 34 degrees F.

This final desired product was then tested and compared to hop flowers from the same lot that were not processed. The results showed that the concentrations of the alpha and beta acids increased with a minimal decrease in the hops-storage-index (HSI). HSI is a way of measuring the shelf life of a hop's flower. It provides an expected loss (percentage) in the desirable alpha acids in the hops flower over a 6-month period when the hop flower is stored at a constant temperature of 68 degrees F. For example, a fresh hop flower that has an amount of desired alpha acids equal to 10% of the whole flower, and an HSI of 25% will have an amount of desired alpha acids equal to about 7.5% when stored for six months at a constant temperature of 68 degrees F. The test results for the final product that was processed through three stages showed a minimal change in the HSI and a significant increase in the percentage of alpha acids relative to the whole final product. Thus, the process significantly increases the amount of desired alpha acid in the final product while causing minimal damage to the alpha acids.

Figure 3:
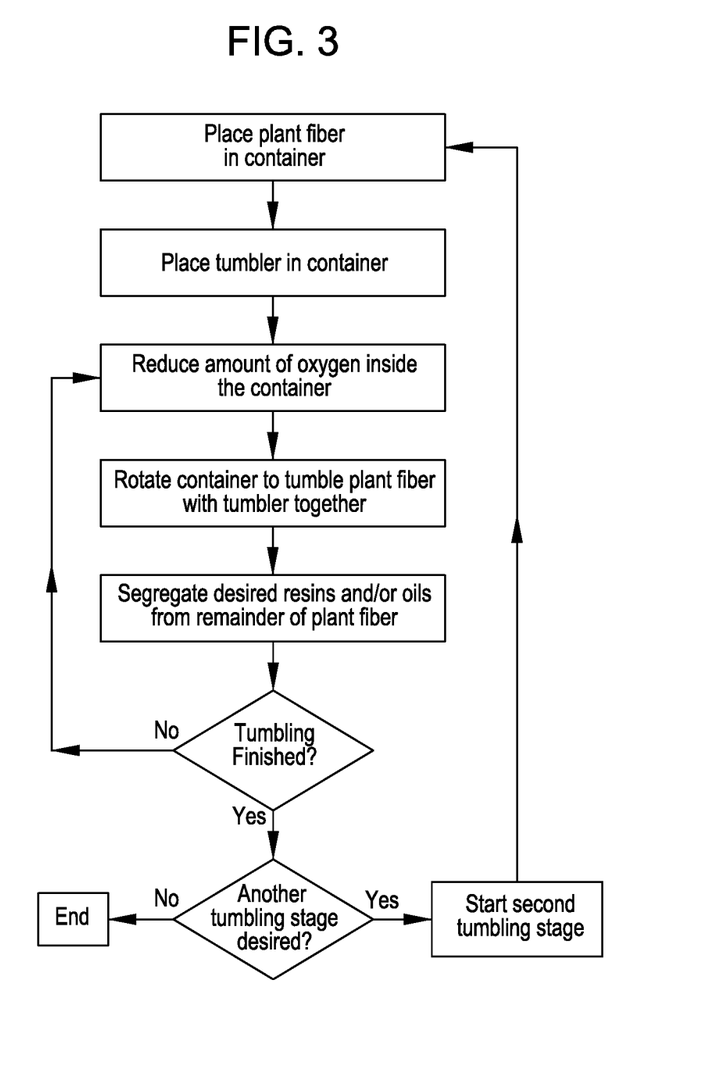
FIG. 3 shows a flow chart of another process for extracting resins and oils from a plant, such as hops, according to another embodiment of the invention.
Figure 4:
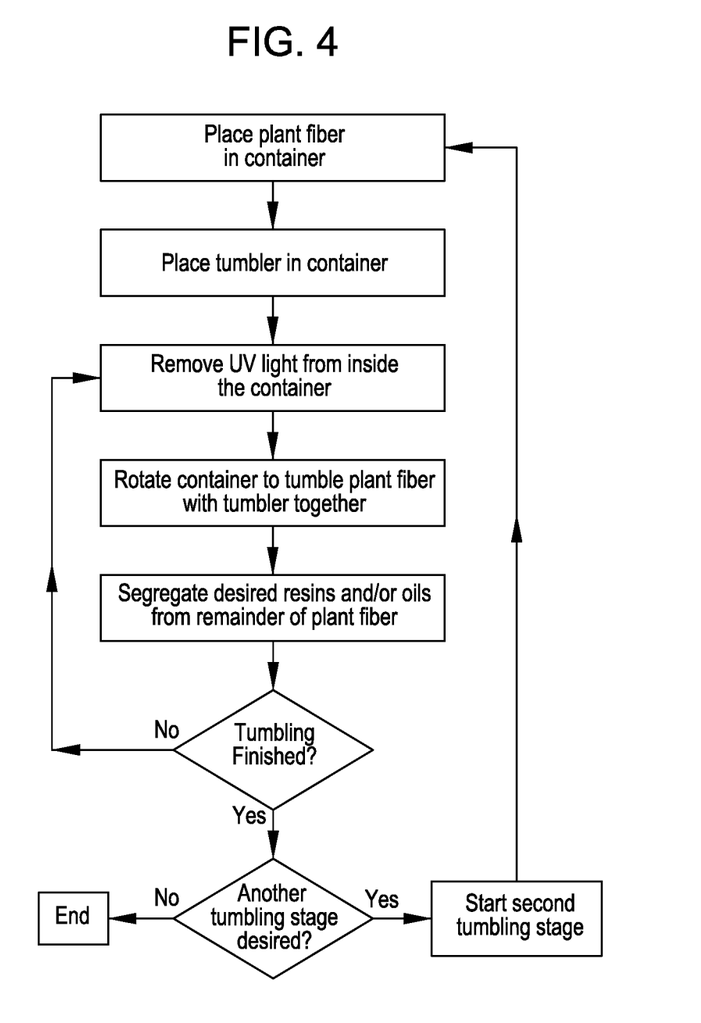
FIG. 4 shows a flow chart of yet another process for extracting resins and oils from a plant, such as hops, according to yet another embodiment of the invention.
Figure 5:
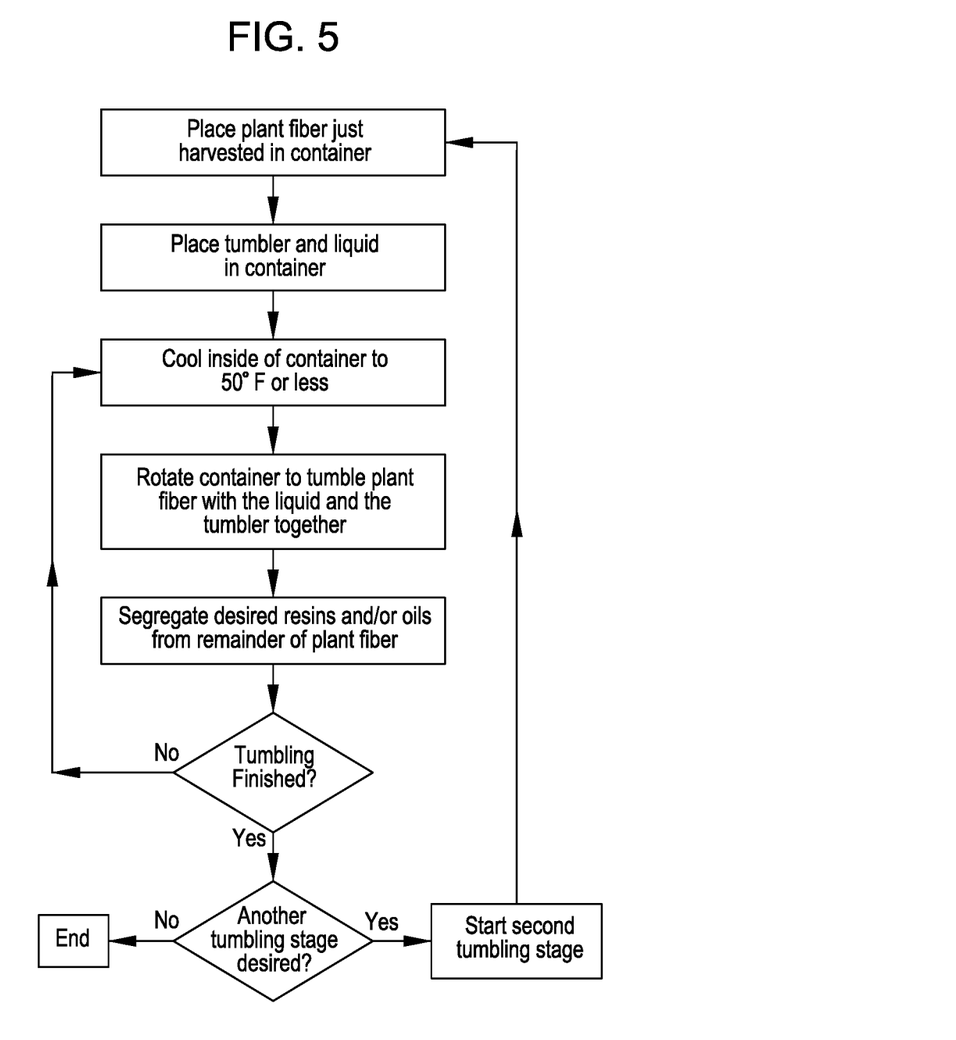
FIG. 5 shows a flow chart of another process for extracting resins and oils from a plant, such as hops, upon harvesting the plant, according to another embodiment of the invention.

Each of FIGS. 3, 4 and 5 shows a flow chart of another process for extracting resins and oils from a plant, such as hops, according to another embodiment of the invention. The process shown in FIG. 3 is similar to the process shown in and discussed in conjunction with FIG. 2, except that tumbling the plant fibers and the tumbler in the container's cavity is done in the absence of elemental oxygen (O) or molecular oxygen ($O_2$). The process shown in FIG. 4 is also similar to the process shown in and discussed in conjunction with FIG. 2, except that tumbling the plant fibers and the tumbler in the container's cavity is done in the absence of ultra-violet light. And, the process shown in FIG. 5 is similar to the process shown in and discussed in conjunction with FIG. 2, except that a liquid is also placed in the container's cavity with the tumbler and the plant fibers and then the three are tumbled/mixed together.

The liquid used in the process shown in FIG. 5 may be any desired liquid. For example, in this and other embodiments the liquid is water, which helps protect the desired essential oils, terpenes and terpenoids from damage during the process. In other embodiments, the liquid may be a solvent that helps separate the desired essential oils, terpenes and terpenoids from the undesired plant fibers by dissolving or weakening the plant fibers' cellular structure. In still other embodiments, the liquid may be a liquid that helps capture and hold the desired essential oils, terpenes and terpenoids by mixing with the desired essential oils, terpenes and or terpenoids.

In embodiments that include tumbling/mixing the plant fibers, tumbler and liquid in the container's cavity, the step of segregating the desired portions of the plant fibers that contain the essential oils, terpenes and terpenoids from the undesired portions of plant fibers may include using a screen with a smaller mesh size than the screen discussed in conjunction with FIG. 2. In addition, the segregating step may include skimming the liquid to remove material that is less dense than the liquid and that is not mixed with the liquid.

Other embodiments are possible. For example, a process for extracting resins and oils from a plant may include any combination of the processes shown in FIGS. 2-5 and discussed in conjunction with them. More specifically, a process may include tumbling plant fibers and the tumbler at a temperature 50 degrees F. or less, and in the absence of elemental oxygen (O) or molecular oxygen ($O_2$). Or, a process may include tumbling plant fibers and the tumbler at a temperature 50 degrees F. or less, in the absence of elemental oxygen (O) or molecular oxygen ($O_2$), and in the absence of ultra-violet light. Or, a process may include tumbling plant fibers and the tumbler with a liquid at a temperature 50 degrees F. or less, in the absence of elemental oxygen (O) or molecular oxygen ($O_2$), and in the absence of ultra-violet light.

Figure 6:
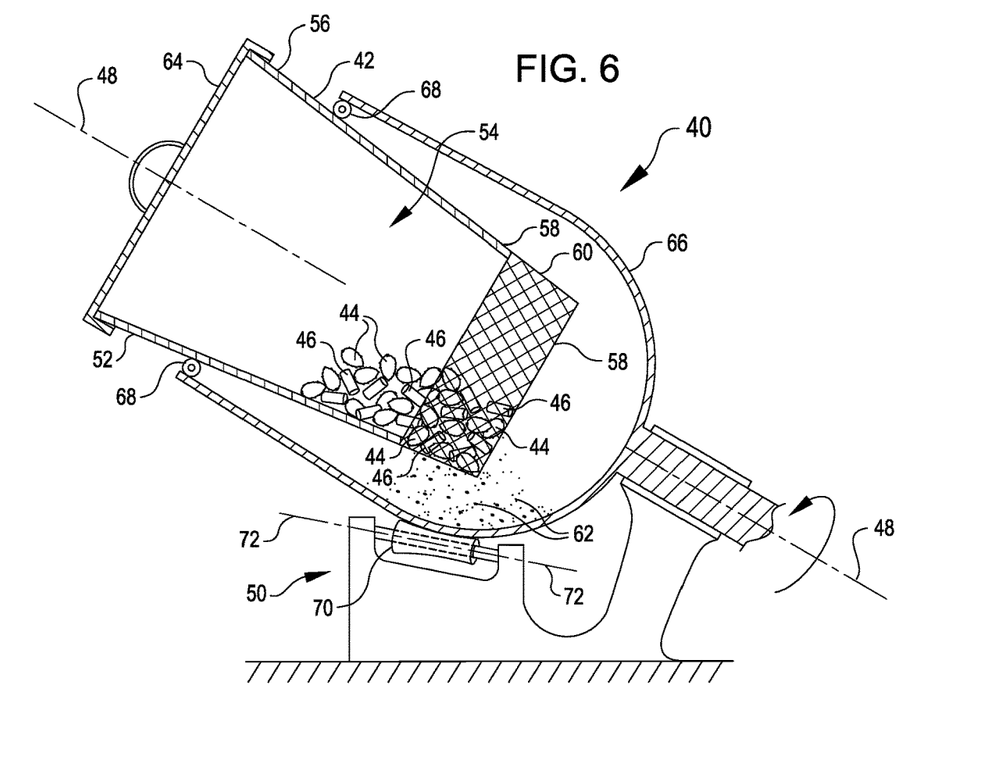
FIG. 6 shows a cross-sectional view of a device to extract resins and oils from a plant, such as hops, according to an embodiment of the invention.

FIG. 6 shows a cross-sectional view of a device 40, according to an embodiment of the invention. The device may be used to implement one or more of the processes shown in, and discussed in conjunction with, FIGS. 2-5 to extract resins and oils from a plant, such as hops. The device 40 includes a container 42 that holds plant fibers 44 (here many but only three are labeled for clarity) and a tumbler 46 (here many but only four are labeled for clarity). The device 40 also includes a motor (not shown) to rotate the container 42 about the axis 48, and a chassis 50 that is coupled to the container 42 and that supports the container 42 while the motor rotates the container 42 about the axis 48. The device also includes a component (shown here as sublimating $CO_2$ pellets that are the tumblers 46) that cools the plant fibers 44 to 50 degrees F. or less while the plant fibers 44 are tumbled with the tumblers 46.

In this and other embodiments, the container 42 includes a body 52 that defines a cavity 54 in which the plant fibers 44 and the tumblers 46 are held while they tumbler and collide with each other. The body 52 has a first region 56 that defines an opening through which the cavity 54 may be accessed, and a second region 58 that includes a screen 60. The screen 60 segregates the desired plant fibers 62 that contain essential oils, terpenes and terpenoids from undesired plant fibers by allowing the desired plant fibers 62 to leave the cavity 54. The container 22 also includes a lid 64 that forms a seal with the container's body 52 when positioned on the body 52. The seal between the lid 64 and the container's body 52 prevents the gas from the sublimating tumblers 46 from escaping between the lid 64 and the body 52. This causes the $CO_2$ gas to generate pressure inside the container 42. When enough pressure is generated, the gas is then directed out through the screen 60. This helps urge correctly sized plant fiber through the screen 60 where it can be easily extracted for future use, or tumbled again in a second stage whose container 22 has a screen 60 with a finer mesh.

In this and other embodiments, the chassis 50 includes a receptacle 66 that holds and rotates the container 42 to tumble the plant fiber 44 and the sublimating tumblers 46. The receptacle 66 also catches and holds the desired plant fibers 62 that contain the desired essential oils, terpenes and terpenoids after they pass through the container's screen 60. The receptacle 66 includes a seal 68 to prevent the $CO_2$ gas from the sublimating tumblers 46 from escaping out from the inside of the receptacle 66, between the container's body 52 and the receptacle 66 where the receptacle releasably holds the container 42. The chassis 50 also includes a roller 70 that contacts the receptacle 66 and supports the receptacle 66 while the motor rotates the receptacle 66 by rotating about the axis 72.

The container 42 and receptacle 66 may include any desired material. For example, in this and other embodiments, the container 22 includes nickel to help promote the preservation of the essential oils, terpenes and terpenoids held by the plant fibers 44. And, the receptacle 66 includes a ceramic coating to more easily extract the desired plant fibers 62. In other embodiments, the container 42 and the receptacle 66 may include other materials.

Figure 7:
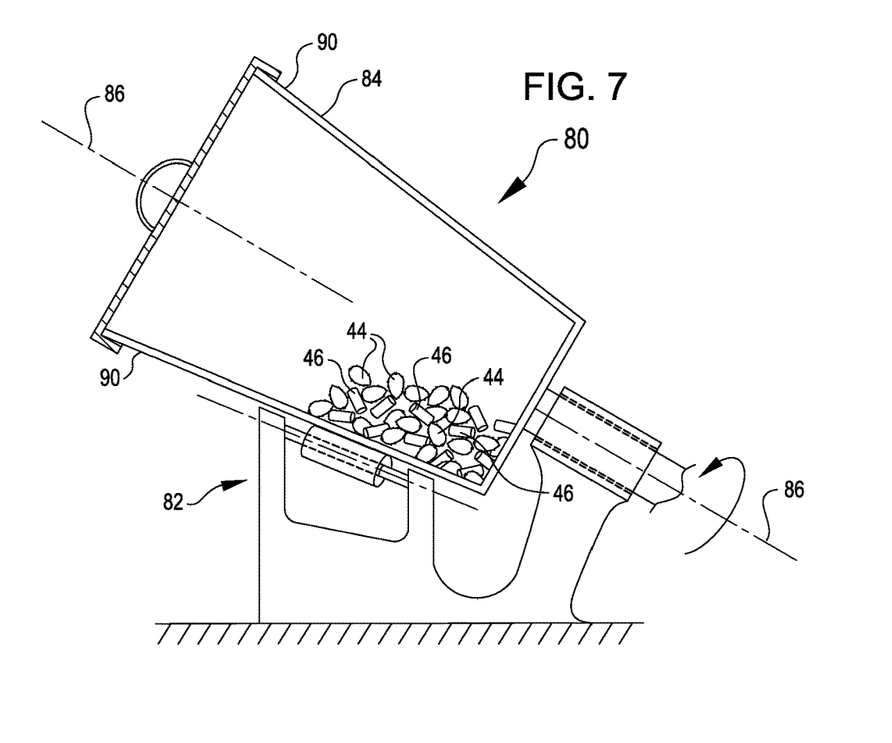
FIG. 7 shows a cross-sectional view of another device to extract resins and oils from a plant, such as hops, according to another embodiment of the invention.

FIG. 7 shows a cross-sectional view of another device 80, according to another embodiment of the invention. The device 80 is similar to the device 40 shown in, and discussed in conjunction with, FIG. 6 except the chassis 82 of device 80 does not include a receptacle. To support the container 84 while the motor (not shown) rotates the container 84 about the axis 86, the roller 88 of the chassis 82 contacts the container's body 90.

The preceding discussion is presented to enable a person skilled in the art to make and use the invention. Various modifications to the embodiments will be readily apparent to those skilled in the art, and the generic principles herein may be applied to other embodiments and applications without departing from the spirit and scope of the present invention. Thus, the present invention is not intended to be limited to the embodiments shown, but is to be accorded the widest scope consistent with the principles and features disclosed herein.

What is claimed is:

1. A method for extracting resins and/or oils from a plant from the Humulus genus comprising:
    (a) tumbling together inside a container one or more tumblers and plant parts containing plant fibers,
        wherein the container has a temperature of less than or equal to 50° F. and an atmosphere that does not include elemental oxygen (O) or molecular oxygen ($O_2$), and
        wherein the one or more tumblers are loose inside the container such that a tumbling motion of the one or more tumblers inside the container is random;
    (b) colliding the one or more tumblers with plant parts to separate one or more portions that contain resins and/or oils from the remainder of the plant fibers; and
    (c) segregating the one or more portions that contain resins and/or oils from the remainder of the plant fibers.

2. The method of claim 1 wherein the atmosphere includes $CO_2$.

3. The method of claim 1 wherein the atmosphere is substantially $CO_2$.

4. The method of claim 1 wherein the one or more tumblers includes $CO_2$ in the solid phase and the atmosphere includes the $CO_2$ gas generated as the $CO_2$ in the solid phase sublimates.

5. The method of claim 1 wherein the plant parts comprise hop flowers.

6. The method of claim 5 wherein the hop flowers contain lupulin glands.

* * * * *